United States Patent [19]

Busko et al.

[11] Patent Number: 5,903,319
[45] Date of Patent: May 11, 1999

[54] METHOD FOR ELIMINATING TEMPORAL AND SPACIAL DISTORTION FROM INTERLACED VIDEO SIGNALS

[75] Inventors: Nicholas Busko, Knoxville; H. Craig Grantham, Jefferson City; Michael J. Tourville; H. Lee Martin, both of Knoxville, all of Tenn.

[73] Assignee: Interactive Pictures Corporation, Oak Ridge, Tenn.

[21] Appl. No.: 08/373,434

[22] Filed: Jan. 17, 1995

Related U.S. Application Data

[63] Continuation-in-part of application No. 08/189,585, Jan. 31, 1994, Pat. No. 5,384,588, which is a continuation-in-part of application No. 08/014,508, Feb. 8, 1993, Pat. No. 5,359,363, which is a continuation-in-part of application No. 07/699,366, May 31, 1991, Pat. No. 5,185,667.

[51] Int. Cl.$^6$ ...................................................... H04N 5/50
[52] U.S. Cl. ........................... 348/607; 348/147; 348/222; 345/427; 382/275; 382/300
[58] Field of Search ............................ 348/36, 147, 578, 348/607, 222, 443; 382/44, 300, 275; 395/137–139; 345/421, 426, 427; H04N 5/50

[56] References Cited

U.S. PATENT DOCUMENTS

| 3,723,805 | 3/1973 | Scarpino et al. | 315/27 GD |
|---|---|---|---|
| 4,125,862 | 11/1978 | Catano | 358/140 |
| 4,152,724 | 5/1979 | Hunter | 358/109 |
| 4,191,967 | 3/1980 | Dansac et al. | 358/113 |
| 4,463,380 | 7/1984 | Hooks, Jr. | 358/160 |
| 4,518,898 | 5/1985 | Tarnowski et al. | 315/371 |
| 4,549,208 | 10/1985 | Kamejima et al. | 358/108 |
| 4,661,855 | 4/1987 | Gülck | 358/225 |
| 4,670,648 | 6/1987 | Hall et al. | 250/216 |
| 4,724,482 | 2/1988 | Duvent | 358/113 |
| 4,728,839 | 3/1988 | Coughlan et al. | 310/112 |
| 4,736,436 | 4/1988 | Yasukawa et al. | |
| 4,751,660 | 6/1988 | Hedley | 364/518 |
| 4,772,942 | 9/1988 | Tuck | 358/87 |
| 4,797,942 | 6/1989 | Burt | 382/41 |
| 4,807,158 | 2/1989 | Blanton et al. | |
| 4,835,532 | 5/1989 | Fant | 340/728 |
| 4,858,002 | 8/1989 | Zobel | 358/98 |
| 4,858,149 | 8/1989 | Quarendon | 364/522 |
| 4,899,293 | 2/1990 | Dawson et al. | |
| 4,918,473 | 4/1990 | Blackshear | 354/81 |
| 4,924,094 | 5/1990 | Moore | 250/334 |

(List continued on next page.)

FOREIGN PATENT DOCUMENTS 2-127877 5/1990 Japan.
WO 82/03712 10/1982 WIPO.

OTHER PUBLICATIONS

English Abstract 2–127877 (A), May 16, 1990, for "Electronic Still Camera Provided with Fisheye Lens" for Japanese Application No. 63–281550.
"Fooling the Eye", Suzanne Oliver, Jan. 16, 1995 (p. 94).

Primary Examiner—Glenton B. Burgess
Attorney, Agent, or Firm—Banner & Witcoff, Ltd.

[57] ABSTRACT

A method and apparatus for the elimination of temporal and spacial distortions from interlaced video signals, particularly those that occur in signals associated with affine transformations. This elimination is particularly of value for signals that have been magnified so as to prevent the visual appearance of reverse movement of moving images. The removal of these distortions is achieved by sequentially inputting the images fields into three field buffers, updating the data in a rotary manner. This data is withdrawn from any two of the field buffers, while the third field buffer is being updated, and averaging the data from the two. When such averaged data is displayed, there is no apparent reverse direction motion to the image. The method and apparatus are applied to a system wherein there is affine transformation to achieve selected pan, tilt, rotation and magnification of images during the correction of distorted images received from a wide angle lens.

17 Claims, 9 Drawing Sheets

U.S. PATENT DOCUMENTS

| | | | |
|---|---|---|---|
| 4,945,367 | 7/1990 | Blackshear | 354/81 |
| 4,965,844 | 10/1990 | Oka et al. | 382/44 |
| 4,987,489 | 1/1991 | Hurley et al. | 358/105 |
| 4,991,020 | 2/1991 | Zwirn | 358/160 |
| 5,005,083 | 4/1991 | Grage et al. | 358/181 |
| 5,020,114 | 5/1991 | Fujioka et al. | 382/44 |
| 5,023,725 | 6/1991 | McCutchen | 358/231 |
| 5,048,102 | 9/1991 | Tararine et al. | 382/41 |
| 5,067,019 | 11/1991 | Juday et al. | 358/160 |
| 5,068,735 | 11/1991 | Tuchiya et al. | 358/209 |
| 5,077,609 | 12/1991 | Manelphe | 358/109 |
| 5,173,948 | 12/1992 | Blackham et al. | 382/44 |
| 5,175,808 | 12/1992 | Sayre . | |
| 5,185,667 | 2/1993 | Zimmermann | 358/209 |
| 5,200,818 | 4/1993 | Neta et al. | 358/87 |
| 5,231,673 | 7/1993 | Elenga | 382/6 |
| 5,396,583 | 3/1995 | Chen et al. . | |

FIG.1A

FIG.1B   FIELD 0 AT TIME = 1/60 s

FIG.1C   FIELD 1 AT TIME = 2/60 s

INTERLACED FRAME

FIG.3B  FIELD 0 AT TIME = 1/60 s

FIG.3C  FIELD 1 AT TIME = 2/60 s

FIG.3D  FIELD 2 AT TIME = 3/60 s

FIG.3E  INTERLACED, TRIPLE FIELD, LINE AVERAGED FRAME

METHOD FOR ELIMINATING TEMPORAL AND SPACIAL DISTORTION FROM INTERLACED VIDEO SIGNALS

This application is a continuation-in-part of U.S. application Ser. No. 08/189,585 filed Jan. 31, 1994, which is a continuation-in-part of U.S. application Ser. No. 08/014,508 filed Feb. 8, 1993, now U.S. Pat. No. 5,359,363, which is a continuation-in-part of U.S. application Ser. No. 07/699,366 filed May 13, 1991, now U.S. Pat. No. 5,185,667.

TECHNICAL FIELD

The present invention relates to a method and apparatus, together with algorithms, for substantially eliminating predetermined temporal and spacial distortion from real-time interlaced video signals, and, more particularly, to the elimination of these distortions from video signals associated with affine transformations in performing pan, tilt, rotation and magnification, of video signals generated from images, for example, perceived from wide-angle lenses. Further, the invention relates to the elimination of visual evidence of the temporal shift caused by single line changes from the input image to the output image that are inherent in dynamic images that have undergone digital magnification.

BACKGROUND ART

During certain processing of interlaced video signals, and particularly those that have been digitized, there is apparent visual evidence of temporal shift upon a display of an image created by those video signals. Portions of certain types of images, for example, visually appear to be moving backward, with this effect being particularly observed when the images are magnified. When the interlaced video image is enlarged, an odd (or even) number of line shifts may occur in the picture elements (pixels). Even though conventional interlaced images refresh their display every field, for example, at sixty times a second, the temporal reversal of output relative to input may be perceptible to a viewer.

One such area in which this temporal (and spatial) shift become apparent is in the systems described in commonly-owned U.S. Pat. Nos. 5,185,667 issued Feb. 9, 1993, 5,313, 306 issued May 17, 1994 and 5,359,363 issued Oct. 25, 1994. The contents of these patents are incorporated herein by reference as to their entire contents.

In the technology described in these patents, video signals are electronically processed for their transformation according to pan and tilt orientation, rotation and magnification so as to view any selected portion of a total video image under selected conditions. Such transformation is generally referred to in the art as "affine transformation." The affine transformation causes single line shifts in the vertical position of pixels which, in an interlaced image, result in a temporal reversal of the display of the transformed dynamic image. Such reversal is disconcerting to some users of the technology of the cited patents.

in order to minimize these effects, these patents teach using magnification on specific fixed increments. In one, wherein the magnification (really minification) is ½x, every other line is discarded which results in a reduction of input image frequency, called fields, from sixty fields per second to thirty fields per second. This removes the time reversal, but at the same time leads to a reduction in the apparent update rate of moving objects in the input image.

Also, it is common to use a 2x magnification, that is, doubling the magnification by doubling the input lines vertically and the number of pixels horizontally. This, however, does not provide an improvement in the reversal problem, and further provides images of objects that appear to have "fingers" or extensions that do not 0have the proper time relationship.

In addition, it is conventional to utilize filters for deinterlacing. However, this has not been applied to the capture, transformation, magnification, rotation and reconstitution of interlaced images for both input and output.

Accordingly, it is an object of the present invention to provide a method for eliminating the temporal shifts that occur during affine transformation of interlaced video images.

Another object of the present invention is to provide apparatus to carry out the present method for eliminating the temporal shifts.

A further object of the present invention is to provide a method for eliminating distortion caused by temporal shifts that occur during transformation of interlaced video images for the purpose of selecting pan and tilt orientation, rotation and magnification of at least a selected portion of the interlaced video images.

It is also an object of the present invention to provide modified apparatus for transforming interlaced video images according to pan and tilt orientation, rotation and/or magnification whereby temporal and spacial shifts that occur during such transformation are eliminated thereby making an output image more satisfactory to a viewer of these output images.

These and other objects of the present invention will become apparent upon a consideration of the drawings set forth below, together with a complete description thereof.

DISCLOSURE OF THE INVENTION

In accordance with one aspect of the present invention, temporal and spatial distortion present in digitized interlaced video signals is removed by inputting the digitized signals sequentially into three or more field buffers in a rotating manner continuously overwriting data in the "oldest" buffer, that is, the buffer containing the oldest stored data. The stored data in the buffers is simultaneously withdrawn, again in sequence, from the two buffers containing the earliest stored data while the next or oldest buffer is being overwritten with new input. In particular, referring briefly to FIG. 2B, the output is generated by selecting successively two vertically adjacent pixels from two temporally adjacent fields (one pixel from each field buffer) and averaging their respective values, the mathematical average value being the single output pixel. For example, the first pixel of the first line (odd lines) will be averaged with the first pixel (which is vertically adjacent thereto) from the second line (even lines) to form the first output pixel, and so on. Upon averaging the pixel data from the two field buffers, successively outputting pixels from the lines of the present and immediately preceding field, for example from upper left of a display to lower right, the output signal produced is substantially absent of temporal and spatial distortion when displayed and viewed on a television receiver.

This method for distortion elimination, and the apparatus for accomplishing the method, is particularly applied to systems wherein affine transformations are performed to obtain pan and tilt orientation, rotation and magnification, from digitized interlaced video signals so as to visually observe selected portions of images as obtained from a wide angle lens.

BEST MODE FOR CARRYING OUT THE INVENTION

Figure 1A:
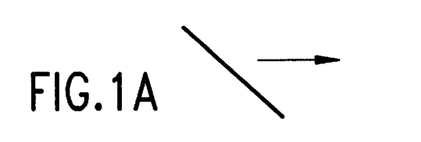
FIGS. 1A through 1E are drawings illustrating how visually-appearing distortion occurs during the processing of affine transformed interlaced video signals.
Figure 1B:
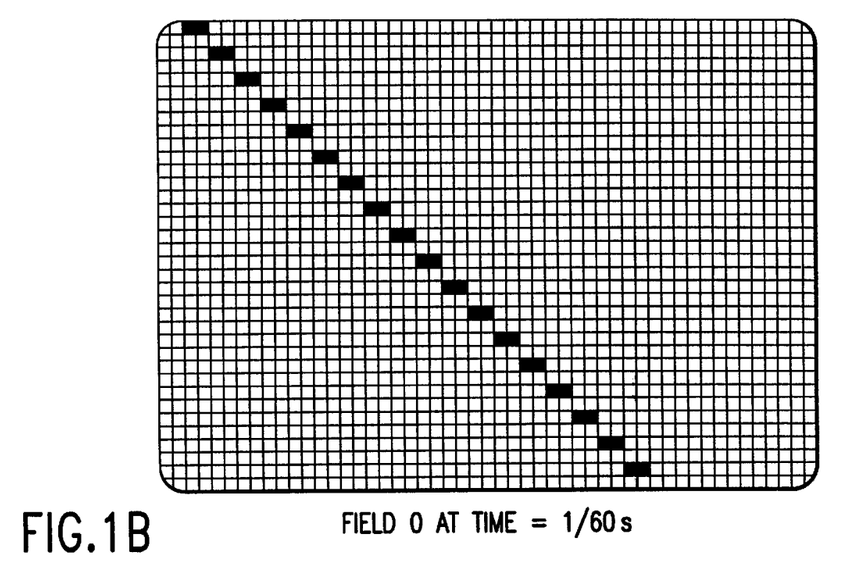
Figure 1C:
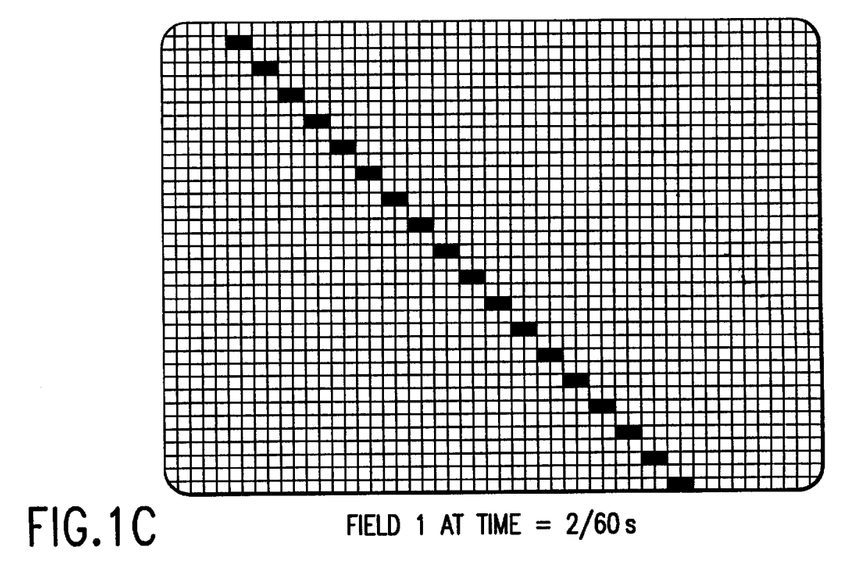
Figure 1D:
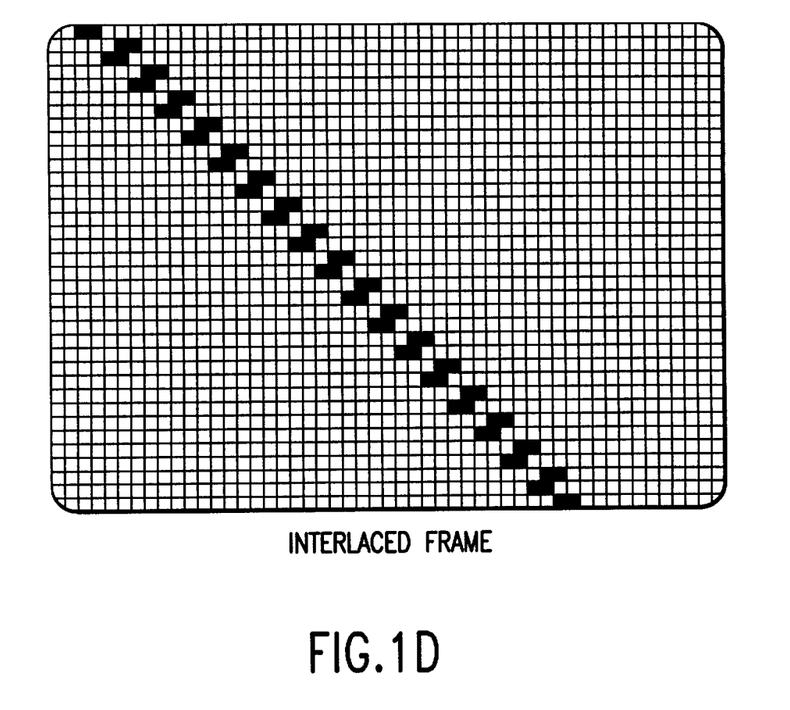
Figure 1E:
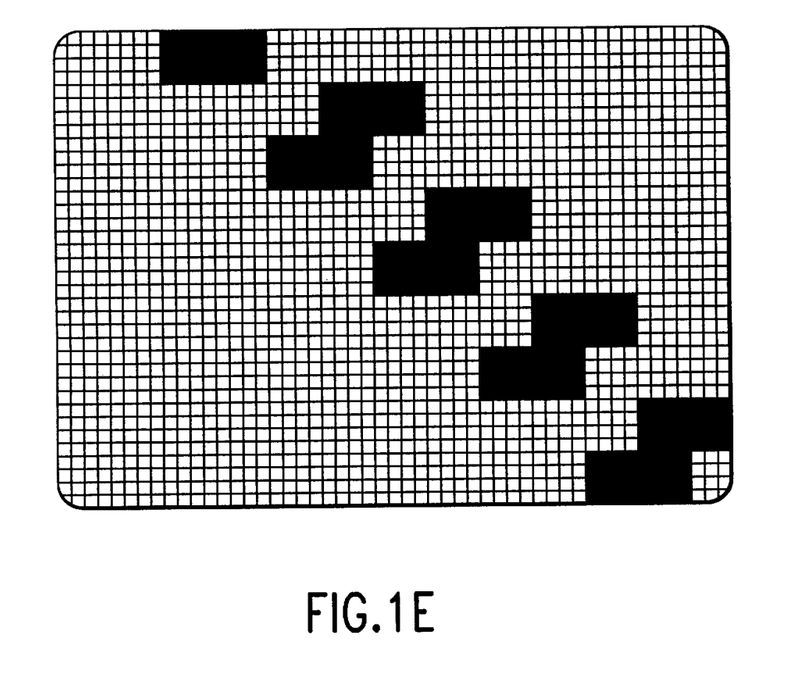

In order to better explain the matter of temporal shift that occurs in the processing of interlaced video signals, reference is made to the four drawings of FIGS. 1A through 1E. FIG. 1A, for example, depicts an image of a straight line moving in the direction indicated. The video image of this line on a screen at a given time would be as indicated in FIG. 1B. Since video images are commonly interlaced, at a given time later (e.g., 1/60 sec later) the video image would appear as in FIG. 1C. However, since the two images are interlaced in video systems of interest, they result in a pattern as depicted in FIG. 1D. When magnified, the result is as in FIG. 1E. Since the image continues to be an ongoing depiction on the video screen, the image can appear to a viewer as moving in a reverse direction. When magnified, this visual distortion caused by temporal shift is very evident and therefore undesirable.

Figure 2A:
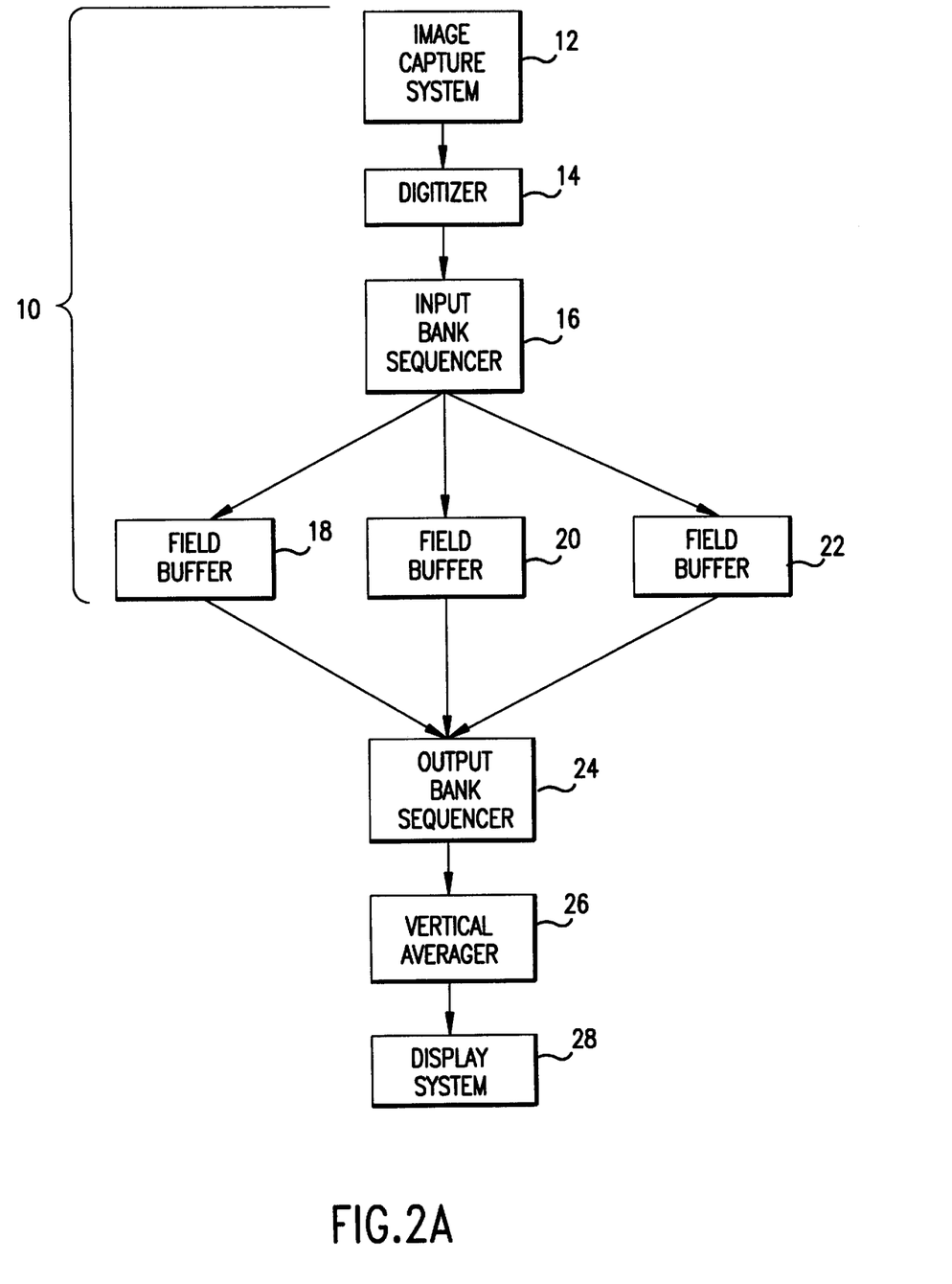
FIG. 2A is a block diagram of a basic circuit for accomplishing the present invention.
Figure 2B:
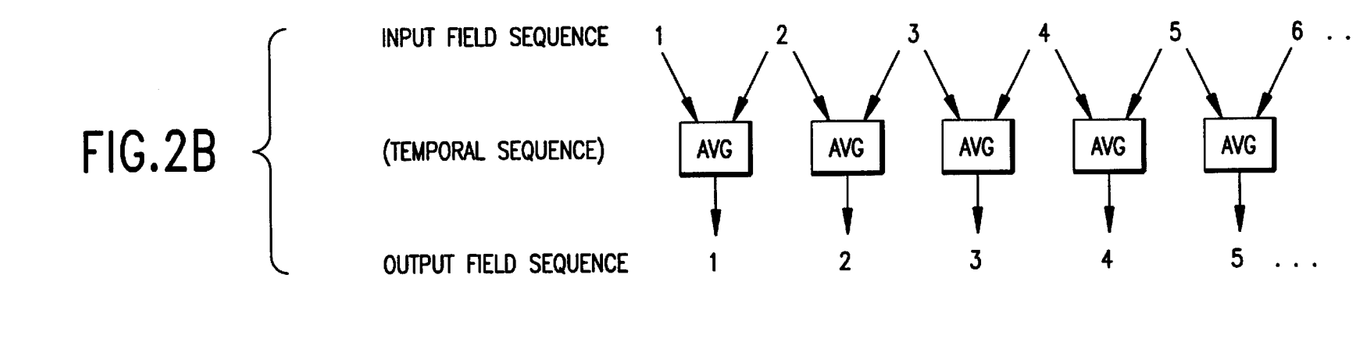
FIG. 2B is a functional diagram showing the method of line averaging of the present invention.

A basic circuit for substantially removing the spatial and temporal distortion is shown at 10 in FIG. 2A and a method therefor is diagrammatically illustrated in FIG. 2B. Any selected system 12 is utilized to capture an image. This can be a video camera, for example. The input can be, however, from a video tape machine or from digital video information stored on computer storage media. A number of standard formats can be used from analog NTSC to PAL to SECAM to High Definition TV (Grand Alliance standard or Japanese MUSE), or totally digital formats.

Figure 2C:
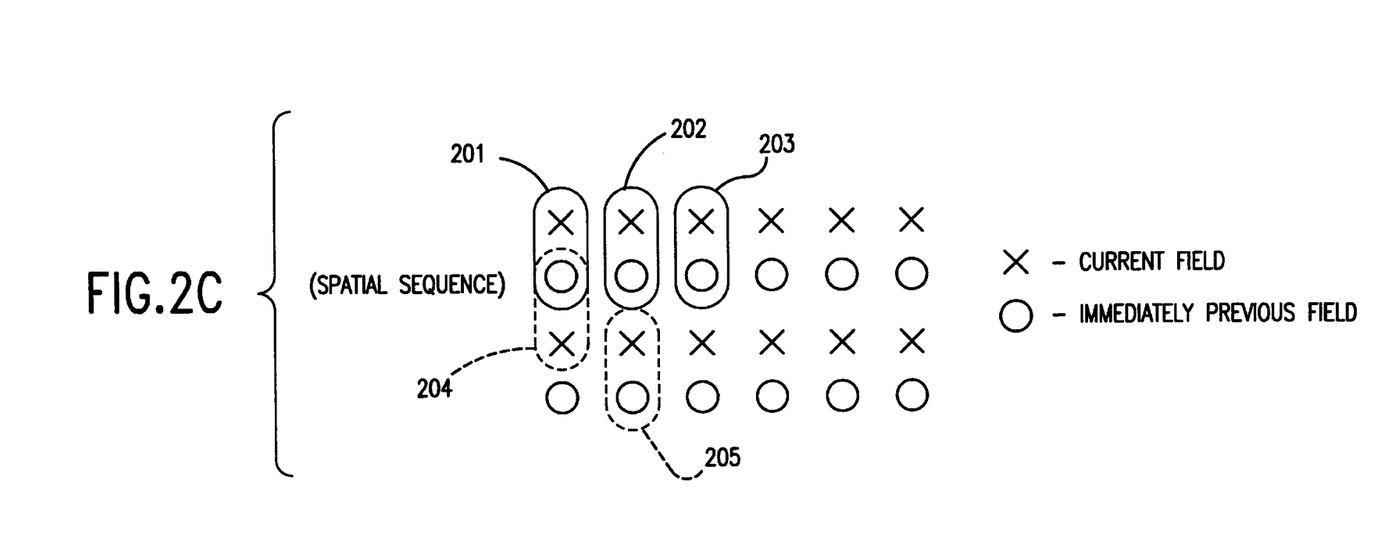
FIG. 2C is a typical video signal raster showing four horizontal lines of interlaced video for explaining the principles of the present invention.

In the process of the image capture the video signals are interlaced. Referring briefly to FIG. 2C, this means that a current field of a plurality of horizontal lines is interlaced with the immediately previous field, ie. every other line containing pixels of the same field shown as X's for the current field or O's for the immediately previous field. The output signal therefrom is digitized, as with the element 14. The digitized signals are fed to an input bank sequencer 16 whereby they are sequentially inputted into three or more identical field buffers 18, 20, and 22 in a rotating manner, overwriting the data in the oldest buffer. Although technology for a sequencer and field buffers will be known by persons skilled in the art, these typically can be created using known FPGA technology, for example, Xilinx XC4005 or XC 3164 or equivalent devices.

An output bank sequencer 24 (typically also an FPGA type device of the types already mentioned) is connected to the output of the three field buffers. This output sequencer withdraws data from any two of the field buffers in a random access fashion while the third or oldest buffer is being loaded with new data. In particular, as will be described further in connection with FIG. 2C, vertically adjacent picture elements are regarded and their data values retrieved. This data withdrawn from the two field buffers (temporally adjacent fields) is averaged in the vertical averager 26 (typically an FPGA device such as a Xilinx XC3120). The resultant averaged signal is then fed into any desired display system indicated at 28. This results in a single field delay in the reporting out of data for the previously transformed field, but any temporal or spatial distortion resulting from, for example, a diagonal line moving across a screen as per FIGS. 1A to 1E is eliminated. Due to this triple field buffer system, and the averaging of two signals, the output display image is substantially devoid of the spatial and temporal shift distortion that would otherwise be observed.

The equations for averaging the picture elements can be derived from the characteristic equation for the general vertical filter:

$$P_{out} = P_{(x, y+n)} C_n$$

where $P_0$ = input pixel t = Range of pixels used on either side of center pixel $C_n$ = an array of coefficients used for each pixel $P_{out} = f(P_{(x,y)})$ where x is fixed and y is variable, that is, in one embodiment, $P_{out} = \frac{1}{2} P_{(x,y)} + \frac{1}{2} P_{(x,y+1)}$ and, consequently, the values of vertically adjacent pixels are averaged from temporally adjacent fields.

The averaging of the signals can be explained using the equation:

$$P_{out(u,v)} = [P_{in(x,y)} + P_{in(x,y+1)}]/2$$

where, $P_{out(u,v)}$ = Output pixel value for a pixel on line v at horizontal position u;

$P_{in(x,y)}$ = Input pixel value f or a pixel on line y at horizontal position x; and $P_{in(x,y+1)}$ = input pixel value for a pixel on line y+1 at horizontal position x.

Referring to FIG. 2B, successive vertical pairs of pixels comprise a pixel from field 1 and a pixel from field 2, field 1 and field 2, being temporally adjacent, which are averaged together to provide an output for field 1. Continuing, field 2 pixels are averaged with field 3, fields 2 and 3 being temporally adjacent in an interlaced image, field 3 with field 4 and so on. The interlacing of lines as per FIGS. 1A–1E which resulted in the distortion shown there is eliminated by this averaging.

Referring to FIG. 2C, there is shown a diagram for showing the averaging of vertically adjacent pixels from temporally adjacent field. There may be a plurality of choices for successive vertical pairs of pixels, one from each of a current and immediately previous field. Starting, for example, with pixel pair 201, this pixel pair represents a directly addressed pixel pair comprising one each of data values for a horizontal row of a current field and a horizontal row from an immediately previous field. They are vertically adjacent; that is, they appear in the same vertical column of an interlaced display, if displayed.

Now the next successive vertical pair may comprise pair 202, it may comprise 203, it may even comprise, according to the present invention, a virtual pixel pair between pair 201 and 202. The point being that many degrees of magnification are possible in the present invention. This magnification may be achieved in this line averaging process as distinguished from magnification which may occur during affine transformation. Greater resolution is achieved by picking successive pairs which are closer together; lesser magnification is achieved by skipping every one, two or more pixel pairs of vertically adjacent pixels.

Looking at the example of picking a high magnification pixel pair between 201 and 202, this may be achieved by averaging values for pixel pairs 201 and 202 together. Thus, the successive vertical pixel pairs are taken at half pixel width increments.

Vertically, the same is true. Pixel pair 204 achieves a greater resolution or degree of magnification than pixel pair 205. Similarly, a weighted pixel pair is possible as between pixel pair 201 and 204 to improve magnification.

One of ordinary skill in the art will readily appreciate that aspect ratios may be varied to output true or intentionally distorted images, as, for example, to output widescreen movies on narrow screen televisions. The addressing of different widths and heights of available corrected (affine transformed) pixels is achieved, for example, to obtain 4×3 aspect ratios from 5×3 aspect ratios. Alternatively, 5×3 aspect ratios may be read out as 4×3 for example for displaying widescreen movies on television raster displays.

Figure 3A:
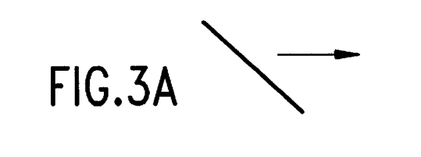
FIGS. 3A through 3F, some of which are similar to FIGS. 1A through 1D, illustrate how the use of the present invention eliminates the distortion.
Figure 3B:
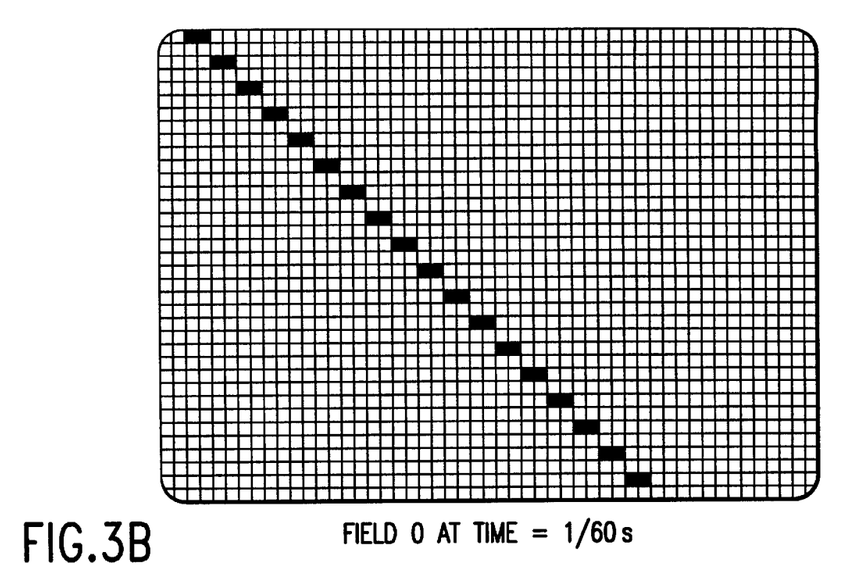
Figure 3C:
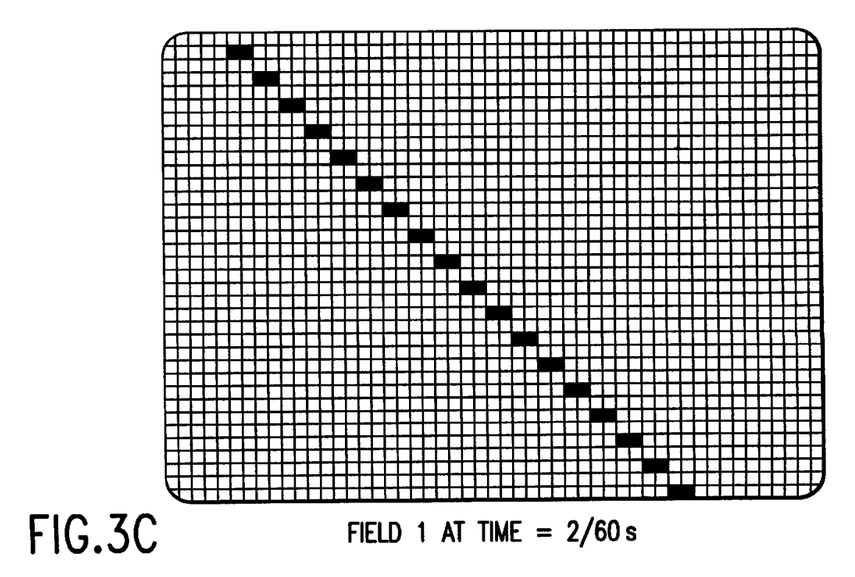
Figure 3D:
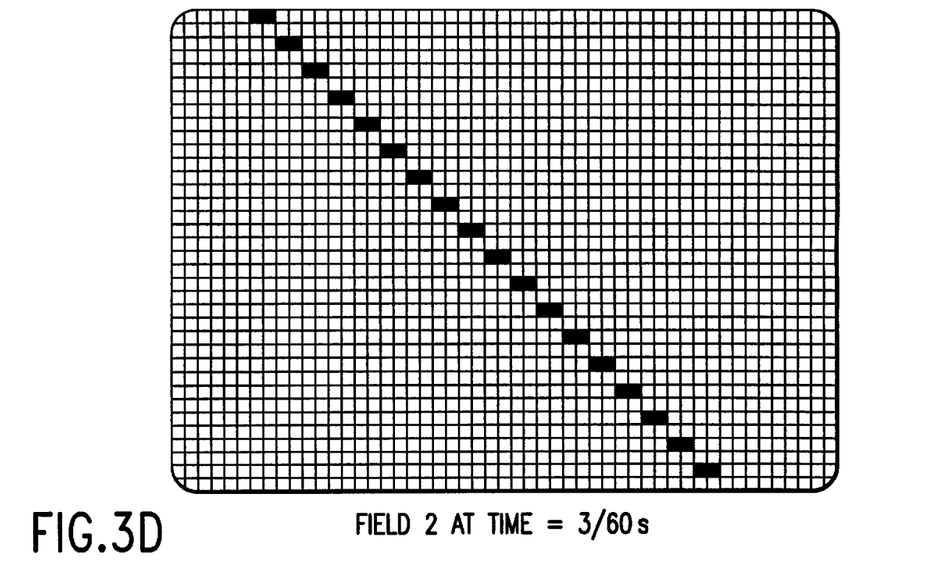
Figure 3E:
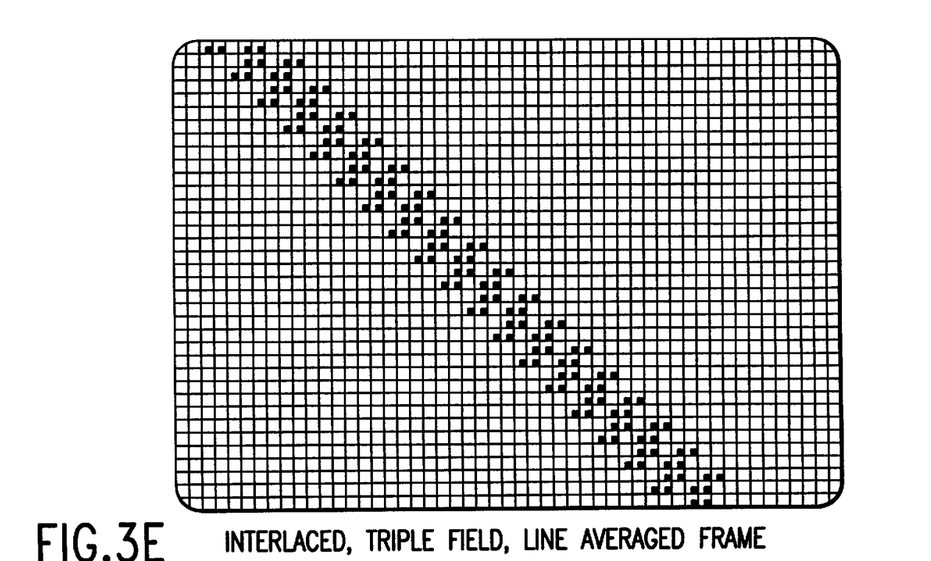
Figure 3F:
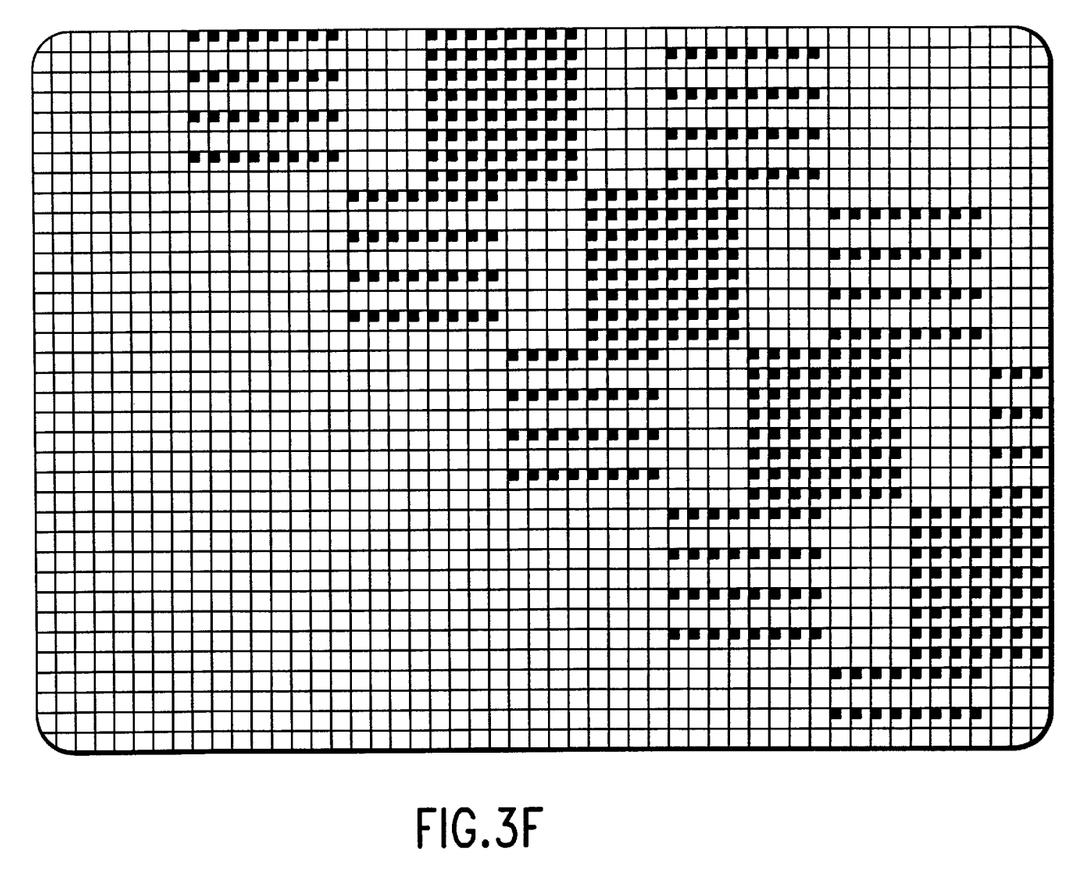

The visual results of the use of three or more buffers, and the sequential averaging of two outputs of the field buffers, is illustrated in the drawings in FIGS. 3A through 3F. As before, this shows the results of a moving diagonal line image of FIG. 3A. FIGS. 3B, 3C and 3D are the video images interlaced (fields) at three different times each field being 1/60th of a second apart as would be the case with conventional National Television Standards Committee format. These fields would be sequentially input to the three field buffers. FIG. 3E depicts the results of the sequential averaging of data in the last two buffers to receive data, while the third buffer is receiving data. This, when magnified as illustrated in FIG. 3F, provides an image that a person would perceive as moving in the same direction as the original line image (FIG. 3A). Thus, the distortion has been eliminated.

Figure 4:
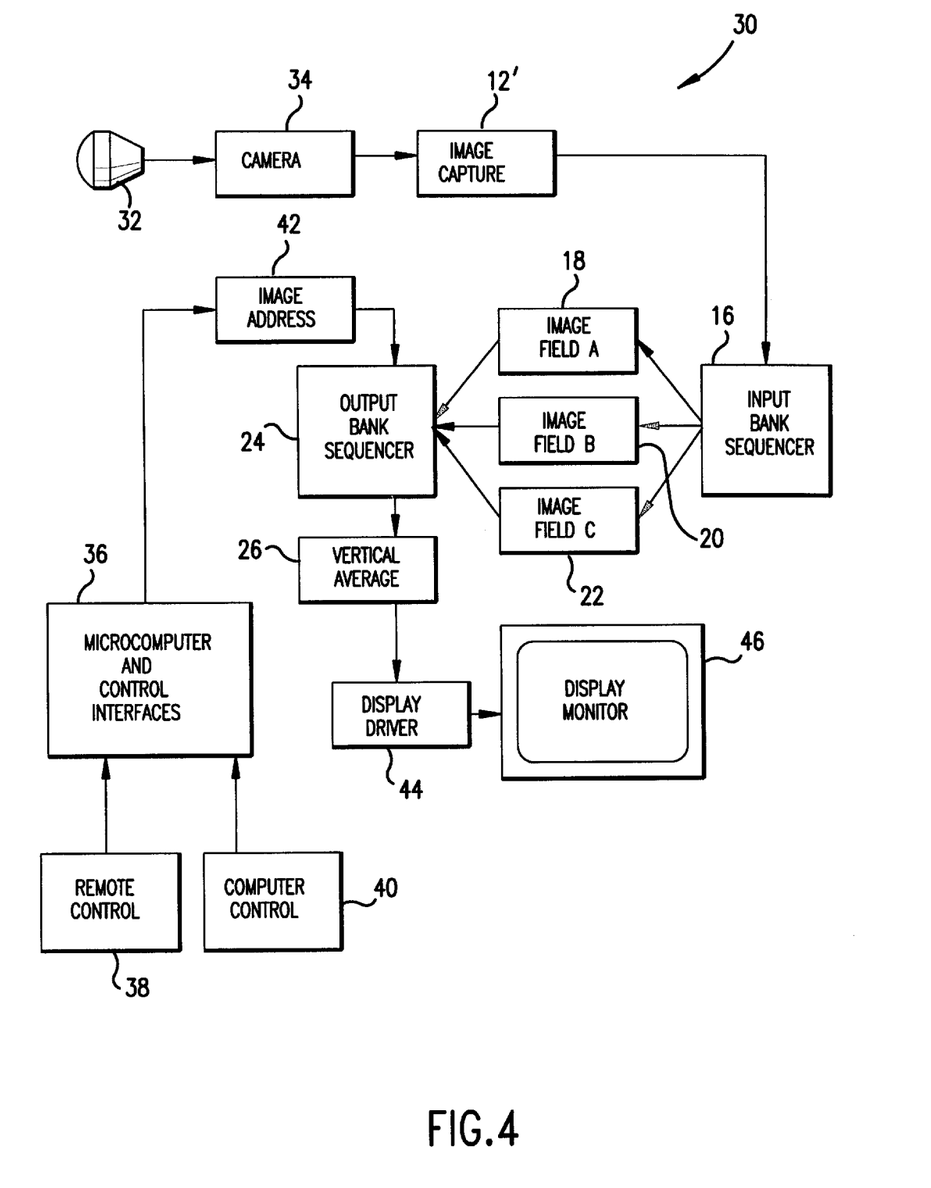
FIG. 4 is a block diagram of a modified circuit for processing interlaced video signals to achieve pan and tilt orientation, rotation and magnification, as well as accomplishing the present invention for eliminating distortion from spatial and temporal shift.

The incorporation of the three or more field buffers and signal averaging into an omnidirectional viewing system is illustrated at 30 in FIG. 4. Certain portions of the circuit will be recognized as being those utilized in the circuits of the afore-cited patents for obtaining a corrected view of selected portions of an image derived using a wide angle lens. Such a system permits electronic pan and tilt orientation, rotation and magnification of these selected portions. The algorithm equations for achieving the necessary transformations are set forth in those patents as well as hereinafter.

In this embodiment 30 of the present invention, an image is viewed by a wide angle lens 32, this being for examples a fish-eye lens. The image (which is distorted in a predetermined manner by the lens or imaging system) is received by a camera unit 34 with its output signal then being fed into an image capture unit 12' which includes a digitizer portion. These digitized signals are then the input to the circuit 10 described with respect to FIG. 2A.

As with the omnidirectional viewing application described in the cited patents, control of the system comes from a microcomputer and control interfaces unit 36. Thus, control can be given through any selected remote controller 38 (as by an operator) or a preselected computer controller 40. Through input as to the desired pan, tilt, rotation and magnification values, and through the algorithm equations cited in the patents, the aforementioned output bank sequencer 24, under control by an image address unit 42, successively withdraws the stored data from two of the three image field buffers 18, 20, and 22. This is indicated by solid lines from field buffers 20 and 22. The broken line from field buffer 18 indicates that this will be sequentially connected in proper time sequence according to control from the sequencer 24. The withdrawn data comprises vertically adjacent pixel values from temporally adjacent fields. The data values are averaged in the averager 26, fed to a display driver 28 which, as depicted herein, has a display driver 44 and display monitor 46.

The specific orthogonal set of transform algorithms used to correct and process any portions of an image are defined by the following two equations, as set forth in the cited patents:

$$x = \frac{R[uA - vB + mR\sin\beta\sin\partial]}{\sqrt{u^2 + v^2 + m^2 R^2}}$$

$$y = \frac{R[uC - vD - mR\sin\beta\cos\partial]}{\sqrt{u^2 + v^2 + m^2 R^2}}$$

where:

A=(cos φcos ∂−sin φsin ∂cos β)
B=(sin φcos ∂+cos φsin ∂cos β)
C=(cos φsin ∂+sin φcos ∂cos β)
D=(sin φsin ∂−cos φcos ∂cos β)

and where:

R=radius of the image circle
β=zenith angle
δ=Azimuth angle in image plane
φ=Object plane rotation angle
m=Magnification
u,v=object plane coordinates
x,y=image plane coordinates Also, it will be understood by one of ordinary skill in the art that the above equations may be substituted by their simplified polynomial approximations in certain applications and the application still obtain satisfactory results thereby. For examples in virtual reality computer game applications, simplified equations based upon fourth or fifth order polynomial approximations may prove economically viable and practical.

Thus, it will be understood that the system 30 illustrated in FIG. 4 operates in substantially the same manner as the systems disclosed in the above-cited patents commonly owned by the Assignee. The difference is in the use of the three or more buffers to receive the image data in rotary sequence, with this image data being withdrawn simultaneously from two buffers for averaging while the third or oldest buffer is being loaded or overwritten with new data. Withdrawal is controlled to obtain the data used for the necessary transform to achieve corrected images. This withdrawn information (data) is averaged prior to display to overcome the temporal and spacial distortion that leads to an apparent reversal of motion in displayed images.

Figure 5:
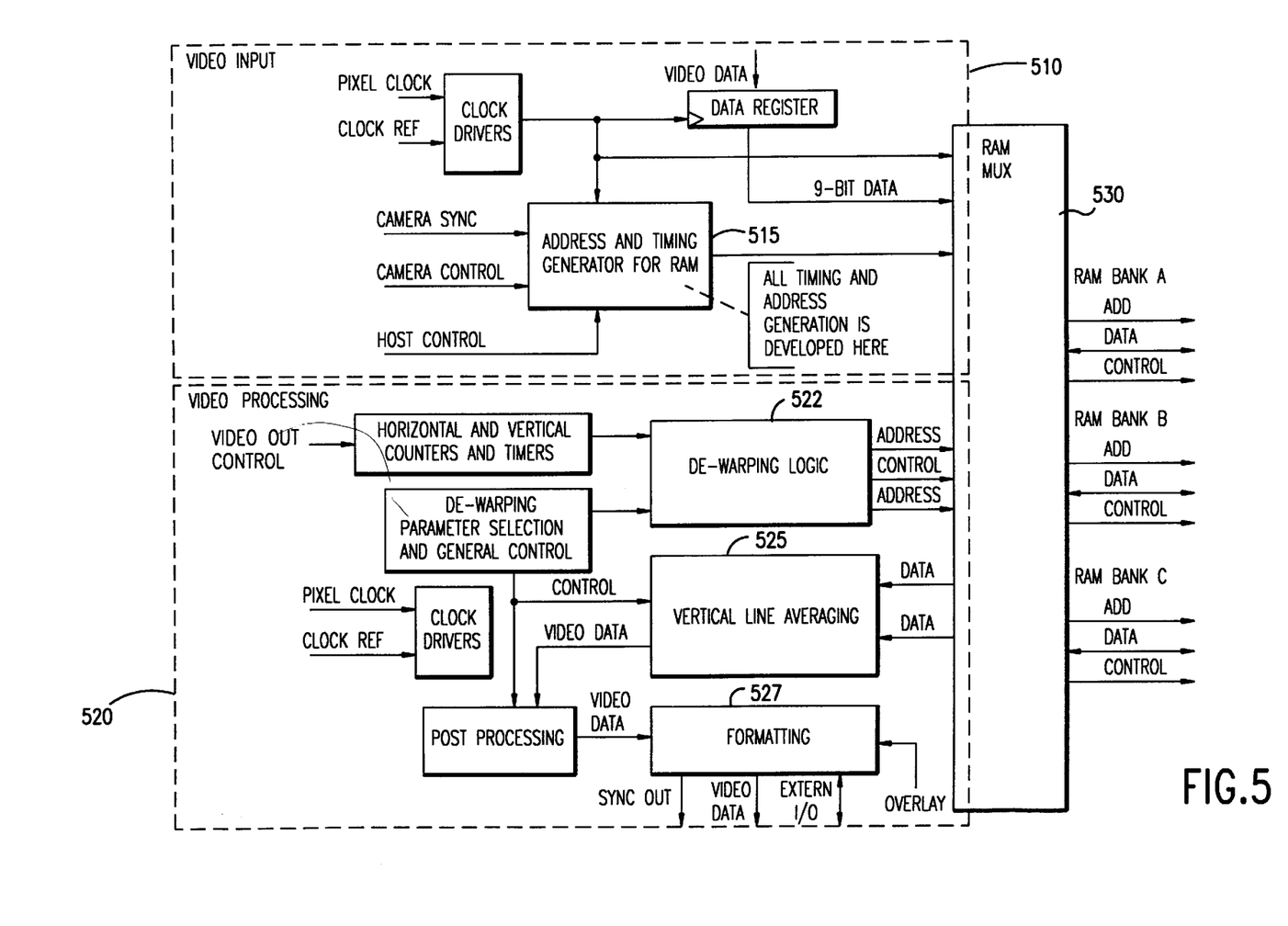
FIG. 5 is a functional block diagram of an application specific integrated circuit embodying the method and apparatus of the present invention.

One implementation of the above-described method and apparatus is in the form of an application specific integrated circuit, functionally shown in schematic form in FIG. 5. Referring to FIG. 5 there is shown a functional block diagram of a distortion correction engine according to the present invention, hereinafter referred to as a video dewarping engine (VDE). As shown, the VDE is divided into three main sections, a video input section 510, a video processing section 520 and a random access memory multiplexer section, RAM Mux 530.

Referring first to the video input section 510 there is shown video data from an external imaging system (off chip), camera, recorder or the like input to a data register driven by clock drivers, clocked by a pixel clock and a clock reference from a clock and control circuit (not shown). There may be multiple such inputs in accordance with the present invention The input video data is stored in buffer RAM banks A, B or C for processing as described above. Two field memories are utilized for data storage for averaging and the third bank for overwriting with new field data. A non-linear scan of pixel data from an array of CMOS active pixel sensors or, alternatively CID or CCD arrays (not shown in FIG. 5) accessed through RAM Mux 530 is described in copending, concurrently filed application Ser. No., incorporated herein by reference. The ASIC depicted in FIG. 5 accepts video data input by whatever means, corrects any predetermined distortion introduced by the imaging system, corrects any temporal or spatial distortion by line averaging as described in the present application, and outputs corrected data in a predetermined format.

In the video input section 510, the clock drivers provide clock drive for address and timing generator 515 for RAM Mux 530 and directly to RAM Mux 530. Address and timing generator 515 also generates timing and addresses for dewarping logic 522. For example, 9-bit resolution video data is input to memory from data registers thereafter via RAM Mux 530. Moreover, the address and timing generator 515 is controlled by control inputs, for example, for selecting an image portion for output as per remote control 38 or computer control 40 (of FIG. 4) here shown as camera sync, camera control and host control leads or data buses. As taught in U.S. Pat. No. 5,185,767, the control input should, at least, provide a viewing angle having zenith and azimuth angle components from a central line-of-sight. Other control input data includes rotation, a distortion inherently correctable in accordance with that described system. As described herein, magnification can be provided in accordance with FIG. 2B during the addressing and scanning process. Thus, without any need for mechanical movement, a camera is panned, tilted rotated, zoomed or the like in accordance with the present invention.

Referring now to the video output or processing section 520, the selected video data is accessed from RAM banks A,B, or C via RAM Mux 530 and operated upon via de-warping logic 522 as required The dewarping logic 522, in turn, is controlled via horizontal and vertical counters and timers and parameter selection and general control sections respectively. The manipulated data is output to vertical line averaging circuitry 525 and forwarded to post-processing circuits. Vertical line averaging 525 is performed as described above. Thereafter, the processed video data is output to formatter circuitry 537. There the data may be selectively, overlaid for example, for captioning or teletext messaging or the like and output in a preselected desired format.

The video processing section 520 receives control input as to which of a plurality of formats in which the output may be provided, for example, from NTSC, PAL, SECAM, HDTV, etc. Moreover, video processing section 520 receives pixel clock and a clock reference in the same manner from a clock and control circuit on board the ASIC (not shown).

From the foregoing, it will be understood by persons skilled in the art that a method and apparatus have been described for eliminating (removing) temporal and spatial effects that occur in transforming interlaced video images. This eliminates the bothersome apparent reverse movement of images, particularly when magnified.

Although certain commercial components are indicated for providing a complete description of the present invention, these are solely for illustration and not for limitation. Rather, the invention is to be limited only by the appended claims.

We claim:

1. A method for substantially eliminating temporal and spatial distortion from interlaced video signals, said method comprising:

converting said interlaced video signals to digital signals;

sequentially inputting said digital signals into three field buffers;

sequentially withdrawing said digital signals from two of said three field buffers during inputting of said digital signals into a third of said three field buffers;

averaging said digital signals withdrawn from said two of said three field buffers; and converting said averaged signals into analog video signals.

2. The method of claim 1 wherein said averaging is according to the equation:

$$P_{out(u,v)} = [P_{in(x,y)} + P_{in(x,y+1)}]/2$$

where:

$P_{out(u,v)}$ = Output pixel value for a pixel on line v at horizontal position u;

$P_{in(x,y)}$ = Input pixel value for a pixel on line y at horizontal position x; and $P_{in(x,y+1)}$ = Input pixel value for a pixel on line y+1 at horizontal position x.

3. The method of claim 1 wherein, during said sequential withdrawal step, picture element values of vertically adjacent picture elements of temporally adjacent fields are successively addressed.

4. A method for substantially eliminating temporal and spatial distortion from digitized interlaced video signals, said method comprising:

sequentially inputting said digitized signals into three field buffers in a rotating manner, overwriting data previously stored in each buffer;

sequentially withdrawing said digitized signals from two of said three field buffers during inputting of said digitized signals into a third of said three field buffers; and averaging said digital signals withdrawn from said two of said three field buffers to provide output signals substantially without said temporal and spatial distortion.

5. The method of claim 1 wherein said averaging is according to the equation:

$$P_{out(u,v)} = [P_{in(x,y)} + P_{in(x,y+1)}]/2$$

where:

$P_{out(u,v)}$ = Output pixel value for a pixel on line v at horizontal position u;

$P_{in(x,y)}$ = Input pixel value for a pixel on line y at horizontal position x; and $P_{in(x,y+1)}$ = Input pixel value for a pixel on line y+1 at horizontal position x.

6. The method of claim 4 wherein during said sequential withdrawal step, picture element values of vertically adjacent picture elements of temporally adjacent fields are successively addressed.

7. A method for substantially eliminating temporal and spatial distortion from distorted interlaced video signals obtained from a wide angle lens and intended for affine transformation to select pan, tilt, rotation and magnification for selected portions of said video signals, said method comprising:

converting said interlaced video signals to digital signals;

sequentially inputting said digital signals into three field buffers, continuously overwriting data in each of said three field buffers;

sequentially withdrawing said digital signals from two of said three field buffers during inputting of said digital signals into a third of said three field buffers, said withdrawal controlled by an algorithm for the affine transformation according to pan, tilt, rotation and magnification;

averaging said digital signals withdrawn from said two of said three field buffers; and converting said averaged signals into analog video signals for the selected portion of input video signals.

8. The method of claim 7 wherein said algorithm is defined by one of the sets of a first set of the following equations:

$$x = \frac{R[uA - vB + mR\sin\beta\sin\partial]}{\sqrt{u^2 + v^2 + m^2 R^2}}$$

$$y = \frac{R[uC - vD - mR\sin\beta\cos\partial]}{\sqrt{u^2 + v^2 + m^2 R^2}}$$

or a second set of equations comprising polynomial approximations of the first set.

9. The method of claim 7 wherein said averaging is according to the equation:

$$P_{out(u,v)} = [P_{in(x,y)} + P_{in(x,y+1)}]/2$$

where:

$P_{out(u,v)}$=Output pixel value for a pixel on line u at horizontal position v;

$P_{in(x,y)}$=Input pixel value for a pixel on line y at horizontal position x; and $P_{in(x,y+1)}$=Input pixel value for a pixel on line y+1 at horizontal position x.

10. Apparatus for substantially eliminating temporal and spatial distortion from interlaced video signals, said apparatus comprising:

a convertor circuit for converting said interlaced video signals to digital signals;

an input sequencer circuit for inputting said digital signals into three field buffers;

an output sequencer circuit for withdrawing said digital signals from two of said three field buffers during inputting of said digital signals into a third of said three field buffers;

an averager circuit for averaging said digital signals withdrawn from said two of said three field buffers; and an output convertor circuit for converting said averaged signals into analog video signals.

11. The apparatus of claim 10 wherein said averager circuit averages said withdrawn digital signals according to the equation:

$$P_{out(u,v)} = [P_{in(x,y)} + P_{in(x,y+1)}]/2$$

where:

$P_{out(u,v)}$=Output pixel value f or a pixel on line v at horizontal position u;

$P_{in(x,y)}$=Input pixel value for a pixel on line y at horizontal position x; and $P_{in(x,y+1)}$=Input pixel value for a pixel on line y+1 at horizontal position x.

12. The apparatus of claim 10 further comprising a visual display unit for displaying said analog video signals.

13. An integrated circuit for use in an imaging system comprising a plurality of random access memories, at least two of which comprise memories for storing first and second fields of video data, a random access memory multiplexer coupled to said random access memories, and a plurality of input and output controllers coupled to said random access memories via said random access memory multiplexer, said output controllers comprising one of a dewarping logic circuit and a vertical line averaging circuit.

14. The integrated circuit of claim 13 further comprising an output formatting circuit for outputting data in accordance with a predetermined format.

15. The integrated circuit of claim 13 wherein said input controller comprises means for inputting video data via the random access multiplexer into the random access memories.

16. The integrated circuit of claim 13, the dewarping logic circuit for correcting an image having a predetermined distortion introduced by an imaging system.

17. The integrated circuit of claim 13, the vertical line averaging circuit for correcting temporal and spatial distortion of an interlaced video image.

* * * * *

UNITED STATES PATENT AND TRADEMARK OFFICE
CERTIFICATE OF CORRECTION

PATENT NO. : 5,903,319
DATED : May 11, 1999
INVENTOR(S) : Nicholas BUSKO et al.

It is certified that error appears in the above-identified patent and that said Letters Patent is hereby corrected as shown below:

Column 9, line 26, claim 8, after the two "equations" insert

-- where:

$A = (\cos\phi\cos\delta - \sin\phi\sin\delta\cos\beta)$
$B = (\sin\phi\cos\delta + \cos\phi\sin\delta\cos\beta)$
$C = (\cos\phi\cos\delta + \sin\phi\cos\delta\cos\beta)$
$D = (\sin\phi\sin\delta - \cos\phi\cos\delta\cos\beta)$ and where:

R = radius of the image circle
$\beta$ = zenith angle
$\delta$ = Azimuth angle in image plane
$\phi$ = Object plane rotation angle
m = Magnification
u,v = object plane coordinates
x,y = image plane coordinates --

Signed and Sealed this

Eighteenth Day of January, 2000

*Attest:*

*Attesting Officer*

Q. TODD DICKINSON

*Commissioner of Patents and Trademarks*